(12) United States Patent
Rauscher et al.

(10) Patent No.: US 9,687,330 B2
(45) Date of Patent: Jun. 27, 2017

(54) DENTAL MEASURING DEVICE FOR THREE DIMENSIONAL MEASUREMENT OF TEETH

(71) Applicant: Qioptiq Photonics GmbH & Co. KG, Gottingen (DE)

(72) Inventors: Helmut Rauscher, Warngau (DE); Ulrich Partheymüller, Holzkirchen (DE)

(73) Assignee: Qioptiq Photonics GmbH & Co. KG, Göttingen (DE)

( * ) Notice: Subject to any disclaimer, the term of this patent is extended or adjusted under 35 U.S.C. 154(b) by 384 days.

(21) Appl. No.: 14/312,876

(22) Filed: Jun. 24, 2014

(65) Prior Publication Data

US 2014/0377716 A1    Dec. 25, 2014

(30) Foreign Application Priority Data

Jun. 24, 2013  (DE) .................. 10 2013 106 555
Apr. 8, 2014   (DE) .................. 10 2014 104 993

(51) Int. Cl.
*A61C 1/00* (2006.01)
*A61C 3/00* (2006.01)
(Continued)

(52) U.S. Cl.
CPC ............ *A61C 19/04* (2013.01); *A61B 5/0088* (2013.01); *A61C 9/006* (2013.01); *A61C 19/004* (2013.01);
(Continued)

(58) Field of Classification Search
CPC ..... A61C 19/04; A61C 19/041; A61C 19/042; A61C 19/043; A61C 19/00; A61C 19/003;
(Continued)

(56) References Cited

U.S. PATENT DOCUMENTS 5,759,030 A * 6/1998 Jung .................... A61B 5/4547
356/405
7,104,792 B2 * 9/2006 Taub .................... A61B 1/0607
433/24
(Continued)

FOREIGN PATENT DOCUMENTS

DE    102006049695 A1    4/2008
DE    102007005625 A1    8/2008
(Continued)

OTHER PUBLICATIONS

Extended European Search Report, Dated Nov. 24, 2014; European Application EP14173676.

*Primary Examiner* — Loan H Thanh
*Assistant Examiner* — Garrett Atkinson
(74) *Attorney, Agent, or Firm* — Peter A. Nieves; Sheehan Phinney Bass & Green PA

(57) ABSTRACT

A dental measuring device for three-dimensional measurement of a patient's teeth having projection means with a projection unit 8 to project a measuring structure onto a tooth to be examined. The device also has a camera to capture a measuring structure projected onto the tooth. According to the present invention, the projection unit has at least one UV light source, wherein the power output from the UV light source is selected or can be selected such that light-curing dental materials can be cured by the effect of the UV light, in such a way that the device can be used or is used for curing light-curing dental materials.

18 Claims, 3 Drawing Sheets

(51) Int. Cl.
*A61C 19/04* (2006.01)
*A61C 9/00* (2006.01)
*A61C 13/15* (2006.01)
*A61B 5/00* (2006.01)
*G01B 11/25* (2006.01)
*A61B 5/103* (2006.01)
*A61B 5/107* (2006.01)

(52) U.S. Cl.
CPC ........ *G01B 11/2531* (2013.01); *A61B 5/1032* (2013.01); *A61B 5/1072* (2013.01); *A61B 5/1077* (2013.01)

(58) Field of Classification Search
CPC ..... A61C 19/004; A61C 19/05; A61C 19/052; A61C 19/06; A61B 5/0088
USPC .......................................... 433/29–31, 68, 72
See application file for complete search history.

(56) References Cited

U.S. PATENT DOCUMENTS

| | | | | |
|---|---|---|---|---|
| 7,286,954 | B2* | 10/2007 | Kopelman | A61B 5/1077 382/128 |
| 8,029,278 | B1* | 10/2011 | Levine | A61C 19/063 433/215 |
| 8,215,954 | B2* | 7/2012 | Levine | A61C 19/063 433/215 |
| 8,591,227 | B2* | 11/2013 | Levine | A61C 19/063 433/215 |
| 9,170,199 | B2* | 10/2015 | Hart | A61B 1/043 |
| 9,291,565 | B2* | 3/2016 | Hart | A61B 1/043 |
| 9,295,537 | B2* | 3/2016 | Cao | A61C 19/003 |
| 2001/0029009 | A1* | 10/2001 | Jung | A61B 5/4547 433/29 |
| 2003/0215767 | A1* | 11/2003 | Taub | A61B 1/0607 433/29 |
| 2004/0254476 | A1* | 12/2004 | Quadling | A61B 5/0066 600/476 |
| 2005/0202363 | A1* | 9/2005 | Osterwalder | A61C 9/0006 433/29 |
| 2005/0234526 | A1* | 10/2005 | Gilhuly | A61B 1/00142 607/86 |
| 2008/0166678 | A1* | 7/2008 | Ramot | A61B 1/24 433/29 |
| 2010/0268069 | A1* | 10/2010 | Liang | G06T 7/521 600/425 |
| 2010/0303341 | A1* | 12/2010 | Hausler | A61B 5/0062 382/154 |
| 2012/0026307 | A1* | 2/2012 | Price | A61C 19/004 348/66 |
| 2012/0064477 | A1* | 3/2012 | Schmitt | A61C 9/0006 433/29 |
| 2013/0053701 | A1* | 2/2013 | Wiest | A61B 5/0059 600/476 |
| 2013/0330684 | A1* | 12/2013 | Dillon | A61B 1/00039 433/29 |
| 2014/0272775 | A1* | 9/2014 | Monty | A61C 9/006 433/29 |

FOREIGN PATENT DOCUMENTS

| | | |
|---|---|---|
| DE | 102007005726 B4 | 8/2008 |
| DE | 10 2007 058 859.5 A1 | 6/2009 |
| DE | 102008017481 A1 | 10/2009 |
| DE | 102008040949 A1 | 2/2010 |
| DE | 10 2008 040 947.2 A1 | 4/2010 |
| DE | 10 2008 054 985.1 A1 | 7/2010 |
| DE | 10 2008 055 158.9 A1 | 7/2010 |
| DE | 102009001086 A1 | 9/2010 |
| DE | 10 2007 054 906.9 A1 | 7/2011 |
| DE | 10 2011 077 564.1 A1 | 12/2012 |
| DE | 10 2011 080 180.4 A1 | 2/2013 |
| EP | 2258254 A1 | 12/2010 |
| JP | 2002267430 A | 9/2002 |
| JP | 2009165831 A | 7/2009 |

* cited by examiner

US 9,687,330 B2

DENTAL MEASURING DEVICE FOR THREE DIMENSIONAL MEASUREMENT OF TEETH

CROSS-REFERENCE TO RELATED APPLICATIONS

This application claims the benefit of German Patent Application No.: 10 2013 106 555.4, filed Jun. 24, 2013, entitled "Dental Measurement Device for Three-Dimensional Measurement of Teeth," which is incorporated by reference herein in its entirety.

FIELD OF THE INVENTION

The invention relates to a dental measuring device of the type mentioned in the preamble of Claim 1 for the three-dimensional measurement of a patient's teeth.

BACKGROUND OF THE INVENTION

Such dental measuring devices, hereinafter referred to briefly as devices, have in general been known and are used prior to or in the course of dental treatments for a three-dimensional measurement of the patient's teeth, so that the materials that will be required in the course of the treatment, by way of example crowns, inlays, bridges or implants, can be prepared on the basis of the measurement results. By way of example, measuring devices have correspondingly been known from DE 10 2007 005 726 B4, DE 10 2006 049 695 A1, DE 10 2007 005 625 A1, DE 10 2008 040 949 A1, DE 10 2007 058 859 A1, DE 10 2008 017 481 A1, DE 10 2008 040 947 A1, DE 10 2008 054 985 B4, DE 10 2008 055 158 A1, DE 10 2009 001 086 A1, DE 10 2011 077 564 A1, DE 10 2011 080 180 B4 and JP 2009-165831 A.

A dental measuring device of this type for the three-dimensional measurement of a patient's teeth has been known from DE 10 2007 054 906 B4. The known measuring device has projection means with at least one projection unit to project a measuring structure onto a tooth to be measured. In this case, the projection unit has a light source which projects a grid as a measuring structure onto the tooth to be measured.

SUMMARY OF THE INVENTION

Embodiments of the present invention provide a dental measurement device for three-dimensional measurement of teeth. Briefly described, the present invention is directed to a dental measurement device for three-dimensional measurement of a patient's teeth, including projection means further including at least one projection unit to project a measuring structure onto a tooth to be examined, and a camera for capturing an image of the measuring structure projected onto the tooth. The projection unit has at least one UV light source, and that the output of the UV light source is selected, or can be selected, such that light-curing dental materials can be cured under the influence of the UV light such that the dental measuring device can be used or is used for curing of light-curing dental materials.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The invention will hereinafter be described in more detail by means of an exemplary embodiment with reference to the attached drawing which depicts a schematic, block diagram of an exemplary embodiment of a dental measuring device according to the present invention. In this connection, each of the features shown in the drawing and described in the claims form the subject matter of the invention, both alone or in any combination with one another, independently of their combination in the claims and their references, as well as independently of their description or representation in the drawing.

DETAILED DESCRIPTION

Figure 1:
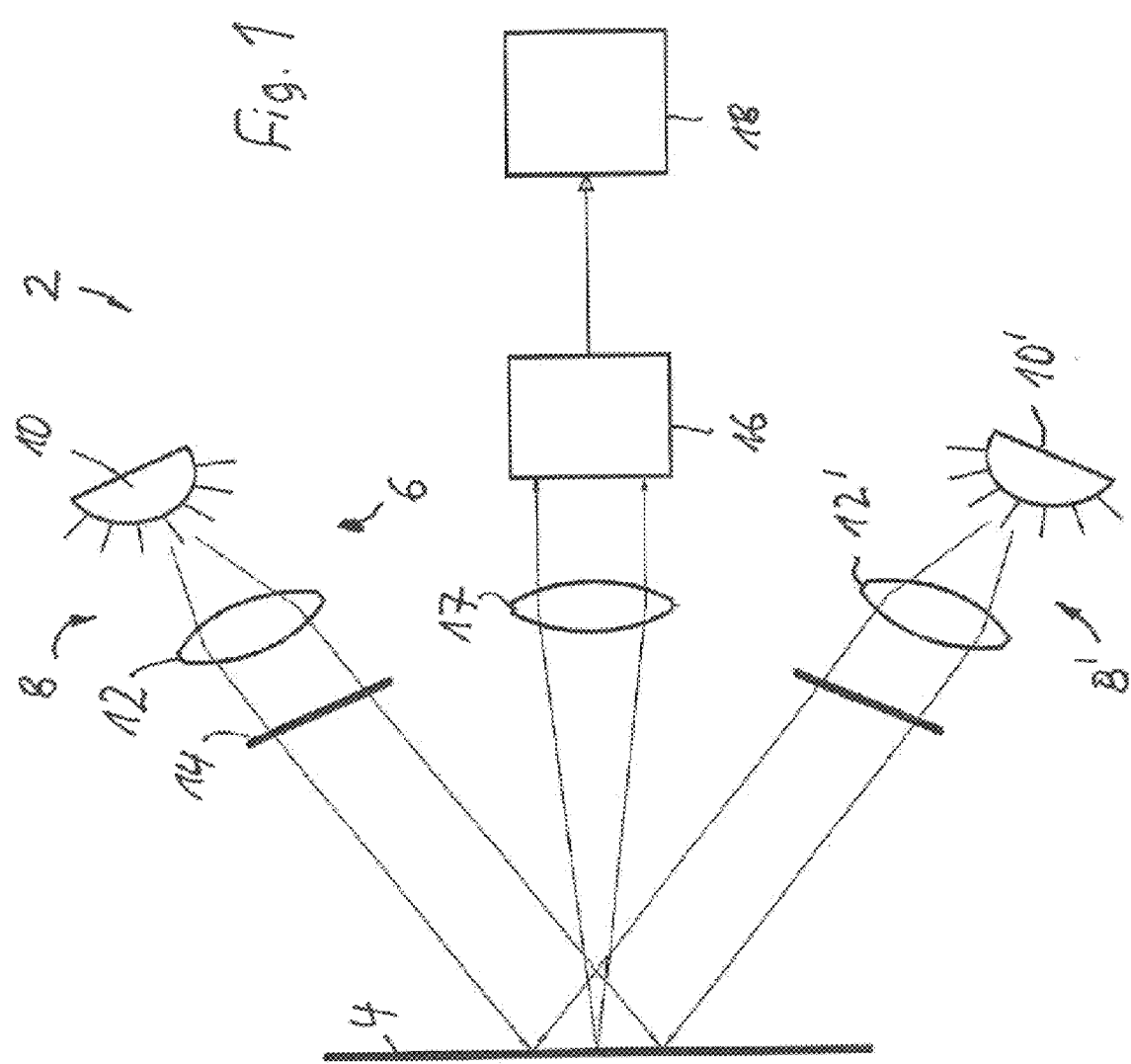
FIG. 1 is a highly schematic block diagram of an exemplary embodiment of a dental measuring device according to the present invention.

The following definitions are useful for interpreting terms applied to features of the embodiments disclosed herein, and are meant only to define elements within the disclosure. No limitations on terms used within the claims are intended, or should be derived, thereby. Terms used within the appended claims should only be limited by their customary meaning within the applicable arts.

The underlying object of the invention is to specify a dental measurement device for three-dimensional measurement of a patient's teeth, whose possible applications are expanded.

The basic idea of the invention consists of modifying the basic equipment used in a dental measuring device for the three-dimensional measurement of teeth such that another task can be carried out by means of the device, namely curing light-curing dental materials. On this basis, the invention provides that the projection unit has at least one UV light source. With regard to the measuring task, namely the three-dimensional measurement of teeth, the use of such a UV light source has the advantage that UV light has a low penetration depth on teeth which increases the measurement accuracy.

Furthermore, the output power of the UV light source is selected, or can be selected, such that light-curing dental materials can be cured in such a way that the dental measuring device can be used, or is used, for curing light-curing dental materials.

Thus, the invention provides a device which is intended and suitable for the three-dimensional measurement of teeth as well as for curing light-curing dental materials.

In this way there is no need for the dentist to have separate devices for the three-dimensional measurement of teeth on the one hand, and for curing light-curing dental materials on the other hand. Rather, both tasks can be carried out with the device according to the present invention. This makes handling easier and reduces the acquisition costs.

According to the present invention, the tasks to be carried out, namely the three-dimensional measurement on the one hand, and curing on the other hand, can be carried out at the same time or consecutively. In a corresponding treatment constellation it is therefore in principle also possible according to the present invention to cure a dental material and to measure a tooth at the same time. However, according to the present invention it is also possible to carry out one task at a time, that is, either a three-dimensional measurement or a cure.

An advantageous further development of the invention provides that the dental measuring device can be switched between a measuring mode and a curing mode, the power output of the UV light source being greater in the curing mode than in the measuring mode. In this embodiment it is possible to work with the specific output of the light source that is required for each task. In the case of a measuring task, for which a lower power output is necessary, it is thus possible to work with a lower power output than for a curing task, for which a higher power output is required. By working with a lower power output in the measuring mode, the patient's exposure to UV light is always kept as low as possible.

The UV light source can be configured in any suitable way. An embodiment which is especially simple and can be produced in a cost-effective manner provides that the light source has at least one light-emitting diode. The corresponding light-emitting diodes which emit light in the UV range are available as relatively simple and cost-effective standard components with a high power output and service life.

An exceptionally advantageous further development of the invention provides that the projection means have at least two projection units, which project from different directions onto the tooth to be measured. In this embodiment a combined effect is obtained in that by using two or more UV light sources, such that on the one hand, the power output that can be applied by the light sources is increased, which is advantageous with respect to curing light-curing dental materials. With respect to curing it is furthermore advantageous that as a result of the radiation from two different directions, shadowing effects which could be caused by teeth in a patient's jaw that are adjacent to the tooth to be measured, are reliably prevented. On the other hand, with respect to the measuring task it is advantageous that the measurement accuracy is increased by using two projection units which project from different directions onto the tooth to be measured. In this embodiment according to the invention it is particularly advantageous to use two projection units, wherein according to the present invention more than two projection units can also be provided.

An advantageous further development of the embodiment mentioned above provides that the projection units are arranged relative to one another such that the projecting measuring structures overlap on the tooth to be measured. Consistent with the invention, and against the background of the method used, namely a shadow projection, the term measuring structure is understood to mean a two-dimensional structure. In this connection, the measuring structure can have a regular configuration, by way of example a regular pattern, or an irregular configuration, by way of example, it can be configured as a point cloud. According to the present invention the measuring structure can consist, for example, of a single line, provided this is sufficient within the framework of the measuring task to be accomplished and the desired measurement accuracy.

With respect to the measuring structure, an advantageous further development of the invention provides that the same line pattern has lines spaced apart from one another, in particular, equidistant lines. An advantageous further development of the embodiment mentioned above combined with an embodiment in which at least two projection units are used, provides that the measuring structure projected by one projection units is oriented relative to the measuring structure projected by another projection unit such that the lines of one measuring structure are perpendicular, or approximately perpendicular to the lines of the other measuring structure. A pattern consisting of mutually perpendicular, or approximately perpendicular, lines thus results, which, when projected onto the tooth to be measured, makes possible a precise assessment of the measurement results in relation to the three-dimensional structure of the tooth to be measured. According to the present invention, the term "approximately perpendicular" is understood to mean that the lines should be considered to be perpendicular to one another within the framework of measurement accuracy.

Another advantageous further development of the invention provides that at least one line pattern has relatively narrow lines, between which relatively broad spaces are formed. When a shadow is projected onto a tooth to be treated, the region of the relatively narrow lines is shadowed, while the UV-light arrives upon the tooth without hindrance in the region between the lines. In this way, it is possible to reliably cure the light-curing materials in spite of the shadowing. As the device according to the present invention is normally accommodated in a hand-held and hand-guided housing, the shadowing effect is compensated by the hand's natural unsteadiness. As the measuring structure can have relatively narrow lines, by way of example having a breadth of <0.5 mm, a normal unsteadiness, which cannot be avoided anyway, is already sufficient for this purpose. In this way the device according to the present invention can be used for curing light-curing dental materials, without it being necessary to move the masks which form the measuring structures closer from the light path of the, or of each, UV light source.

The use of UV-light and thus the provision of a UV light source in a dental measuring device for measurement purposes has an independent inventive significance.

According to the present invention, the use of a dental measuring device for a three-dimensional measurement of the teeth of a patient, the dental measuring device having at least one UV light source, is provided for curing of light-curing dental materials.

The dental measuring device according to the present invention can also be configured to measure the distance between the device and a patient's tooth to be measured. By detecting the distance to the tooth or teeth to be examined, and previously knowing the output power of the UV light source to be detected by appropriate means, the energy input by the UV light can be detected or at least estimated. After applying a predefined amount of energy, the device can then output, for example, a signal to the operator, so that the treatment can be terminated when the predefined or required energy has been applied, and the patient is thus not unnecessarily exposed to UV light.

FIG. 1 shows a highly schematic block diagram of a measuring device 2 which is used for three-dimensional measurement of a patient's teeth and which will hereinafter also be designated briefly as device 2. A tooth to be measured is symbolized by a plane 4 in FIG. 1.

The measuring device 2 has projection means 6 which have a projection unit 8. According to the present invention, it is basically sufficient if the projection means 6 have a single projection unit 8. In the shown exemplary embodiment, another projection unit 8' is provided in addition to the projection unit 8, the projection units 8, 8' projecting onto the tooth from different directions. Exclusively the configuration of the projection unit 8 will be hereinafter described in more detail. The projection 8' unit is configured accordingly, and its components are designated with reference numerals that match the reference numerals of the projection unit 8.

The projection unit 8 has a light source which, according to the present invention is formed by a UV light source 10 that in this exemplary embodiment has at least one light-emitting diode. An illumination lens 12 is arranged in the light path downstream of the UV-light source, which hereinafter will also be designated briefly as the light source. A mask 14 is arranged downstream of the illumination lens 12, which defines a measuring structure as a kind of diapositive, which in this exemplary embodiment is formed by a pattern of equidistant lines (cf. FIG. 2) and is projected onto the tooth to be measured within the framework of a shadow projection.

In the shown exemplary embodiment, the projection units 8, 8' are arranged relative to one another such that the respectively projected measuring structures overlap on the tooth to be measured, namely in the manner of a grid structure. This grid structure is captured by a camera 16 with an upstream observation lens 17, wherein the camera 16 can capture still or moving images. The image or images captured by the camera 16 are sent to evaluation means 18, wherein the three-dimensional structure of tooth 4 can be calculated by the evaluation means 18 on the basis of the distortion of the grid structure. The way in which the captured images are evaluated within the framework of a shadow projection to deduce the three-dimensional structure of a tooth therefrom is in general known to a person skilled in the art and it is therefore not described in more detail.

According to the present invention, the projection unit has at least one UV light source, wherein the output power of the UV light sources 10, 10' is selected, or can be selected, such that light-curing dental materials can be cured in such a way that the device 2 can be used, or is used, for curing of light-curing dental materials.

In this connection, a combined effect is obtained in the shown exemplary embodiment as, firstly, by using two light sources 10, 10' the light output that can be applied to the tooth 4 or a related dental material is increased, which is advantageous with regard to a reliable cure. And secondly, the measurement accuracy is especially good owing to the use of two projection units 8, 8'.

According to the present invention, it is possible to configure the device 2 such that it can be switched between a measuring mode and a curing mode; the output power of the UV light sources 10, 10' being greater in the curing mode than in the measuring mode. According to the present invention, it is, however, also possible to configure the output power of the UV light source 10, or of the UV light sources 10, 10', in the shown exemplary embodiment from the outset such that they are sufficient for reliably curing of light-curing materials.

Figure 2:
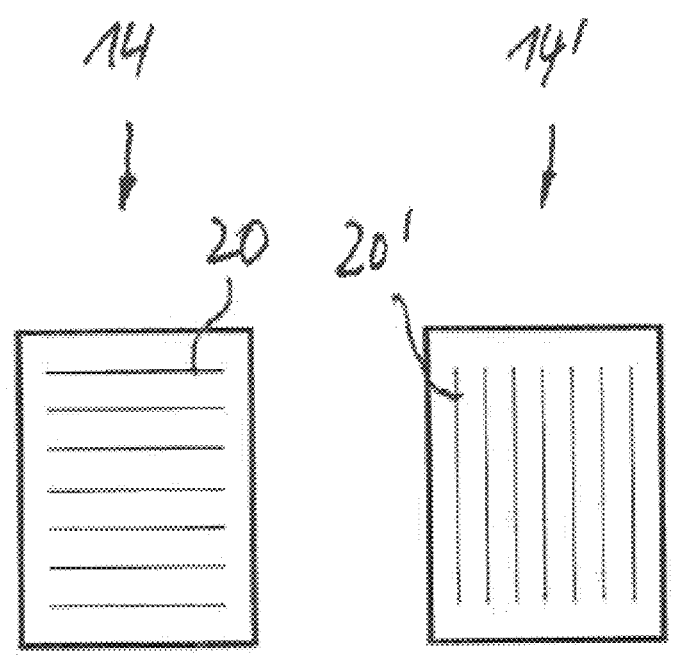
FIG. 2 shows masks used in the device according to FIG. 1 as measuring structures for shadow projection.

FIG. 2 shows a view of the masks 14, 14', wherein it is evident that each of the masks 14, 14' define a measuring structure which consists of a pattern of equidistant lines, of which only one line 20 or 20', respectively, is identified in FIG. 2. As is furthermore apparent from FIG. 2, the measuring structures in the shown exemplary embodiment are oriented relative to one another such that the lines 20 of the mask 8 are perpendicular to the lines 20' of the mask 8', so that a grid pattern results from overlapping of the measuring structure in the shadow projection.

Figure 3:
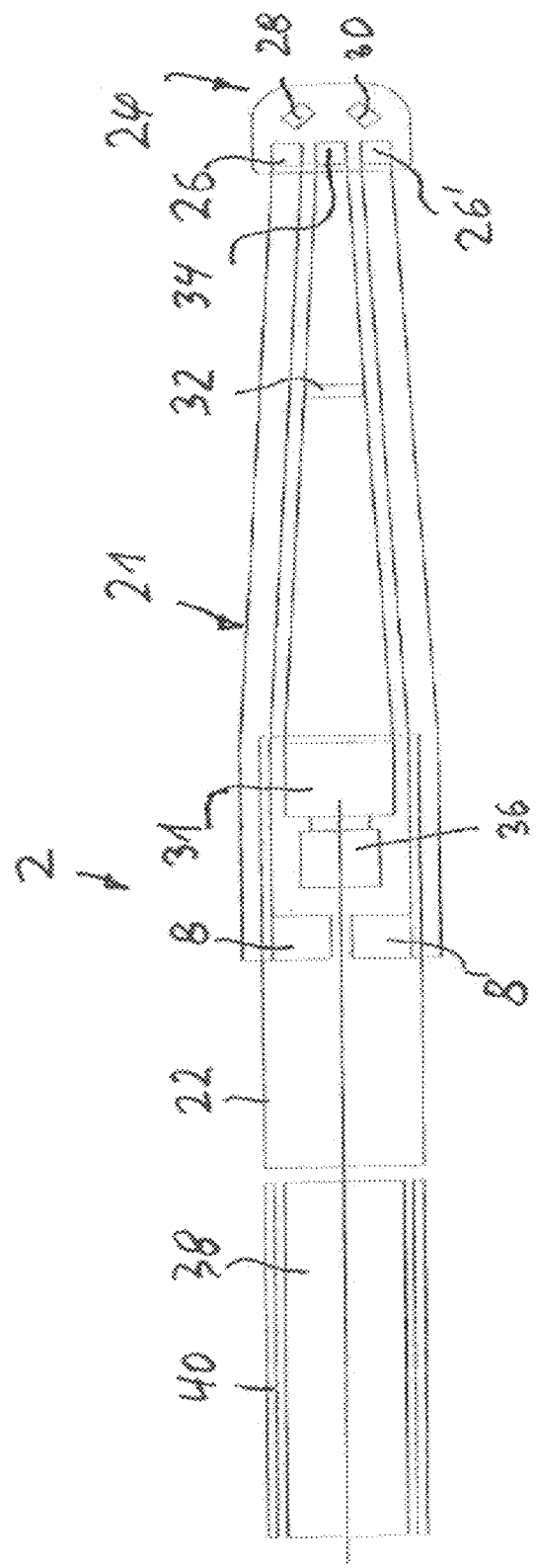
FIG. 3 is a schematic exemplary application of a dental measuring device according to the present invention in the form of a dental camera.

FIG. 3 depicts a highly schematic, exemplary application of a dental measuring device 2 according to the present invention in the form of a dental camera, which has a hand-held and hand-guided housing 22. The components of the dental measuring device 2 according to the present invention are only schematically sketched in FIG. 3.

The projection units 8, 8' together with the corresponding UV light source are accommodated in the central part of the housing 22. Its light path leads to a camera head 24, on which exit prisms 26, 26' are arranged which direct the light path of the projection units 8, 8' such that, by way of example, the constellation shown in FIG. 1 is obtained. To illuminate a point observed with the dental camera 21, illumination means can be provided on the camera head 24, by way of example, in the form of two preferentially white LEDs 28, 30.

An image sensor, by way of example a CMOS image sensor can likewise be arranged in the central part of the housing 22. A liquid lens 32 can be associated with the image sensor 32, by way of example as an observation or imaging lens, the light path of the imaging lens being directed via an exit prism 34 onto a point to be measured.

With these components, the dental camera 31 shown in FIG. 3 is suitable for the three-dimensional measurement of teeth as well as for curing of light-curing dental materials, as has already been previously described with reference to the invention.

The imaging sensor 31 can be used not only for measuring purposes within the framework of a shadow projection according to the present invention, but also for observation purposes. Thus, the dental camera 21 provides imaging as a further functionality. If desired, other functionalities can still be added to the dental camera 21. By way of example, a color sensor 36 can be added, for example in the form of a semiconductor color sensor in order to determine the tooth color by means of the color sensor 36 and, where required, in combination with the image sensor 31.

It is not apparent from the drawing, and it is therefore described here that the data transmission from the dental camera 21 to the display, storage or other devices is wireless. A battery, for example, a lithium polymer battery 38 is provided as a power supply to the components of the dental camera 21, which can be charged via an external inductive charging coil 40 shown in FIG. 3. In this way, the battery 38 can be charged in a contactless manner. The subject matter of the application thus also is a dental camera powered by means of a battery, which is charged with an inductive charging coil in a contactless manner.

If desired or necessary, according to the respective requirements, at least one position and/or acceleration sensor can be provided on the dental camera, in particular on the camera head 24. In this way any changes in the position of the camera head 24 can be detected and the information obtained therefrom can be used in the evaluation of the data obtained by means of the dental camera 21. The provision or use of at least one position and/or acceleration sensor on a dental camera likewise has an independent inventive significance.

Thus, the subject matter of the invention is also a dental camera with at least one position and/or acceleration sensor. According to the present invention, a position sensor is understood to mean any sensor which can sense a change and/or changes in the position of the dental camera 21 and/or in particular its camera head 24.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A dental device for three-dimensional measurement of a patient's teeth and curing of light-curable dental materials, comprising:
a hand held and hand guided housing further comprising:
at least one projection unit to project a measuring structure onto a tooth, wherein the measuring structure includes lines or points;
a camera to capture an image of the measuring structure projected onto the tooth;
wherein the at least one projection unit comprises a light source configured to be directed by the hand held and hand guided housing to illuminate the tooth; and
a lens in a light path downstream of the light source, wherein the output of the light source is configurable to switch between a curing mode sufficient to cure the light-curing dental materials, and a measuring mode to measure the tooth with the measuring structure.

2. The dental measuring device according to claim 1, wherein the output power of the light source is configured to be greater in the curing mode than in the measuring mode.

3. The dental measuring device according to claim 2, wherein the light source has at least one light emitting diode.

4. The dental measuring device according to claim 2, wherein the projection means has at least two projection units, which project from two different directions onto the tooth to be measured.

5. The dental measuring device according to claim 2, wherein at least one measuring structure has a line pattern consisting of lines spaced apart from one another or a point cloud.

6. The dental measuring device according to claim 1, wherein the light source comprises a light emitting diode.

7. The dental measuring device according to claim 6, wherein the projection means has at least two projection units, which project from two different directions onto the tooth to be measured.

8. The dental measuring device according to claim 6, wherein at least one measuring structure has a line pattern consisting of lines spaced apart from one another or a point cloud.

9. The dental measuring device according to claim 1, wherein the housing comprises a first projection unit configured to project a first measurement structure onto the tooth from a first direction and a second projection unit configured to project a second measurement structure onto the tooth from a second direction.

10. The dental measuring device according to claim 9, wherein first measurement structure overlaps the second measuring structure.

11. The dental measuring device according to claim 10, wherein at least one measuring structure has a line pattern consisting of lines spaced apart from one another or a point cloud.

12. The dental measuring device according to claim 9, wherein at least one measuring structure has a line pattern consisting of lines spaced apart from one another or a point cloud.

13. The dental measuring device according to claim 1, wherein at least one measuring structure has a line pattern consisting of lines spaced apart from one another or a point cloud.

14. The dental measuring device according to claim 13, wherein the measuring structures of the projection units are oriented relative to one another such that the lines of the measuring structure projected by one of the projection units are perpendicular to the lines of the measuring structure projected by the other projection unit.

15. The dental measuring device according to claim 14, wherein at least one line pattern has relatively narrow lines, between which relatively broad intermediate spaces are formed.

16. The dental measuring device according to claim 13, wherein at least one line pattern has relatively narrow lines, between which relatively broad intermediate spaces are formed.

17. The dental measuring device according to claim 1, wherein the light source comprises an ultraviolet light source.

18. The dental measuring device according to claim 1, wherein the housing further comprises an exit prism.

* * * * *